United States Patent
Ashman

[11] Patent Number: 5,403,316
[45] Date of Patent: Apr. 4, 1995

[54] TRIANGULAR CONSTRUCT FOR SPINAL FIXATION

[75] Inventor: Richard B. Ashman, Dallas, Tex.

[73] Assignee: Danek Medical, Inc., Memphis, Tenn.

[21] Appl. No.: 159,827

[22] Filed: Dec. 2, 1993

[51] Int. Cl.⁶ .............................................. A61B 17/56
[52] U.S. Cl. ...................................................... 606/61
[58] Field of Search ...................... 606/61, 60, 69, 59, 606/72, 73

[56] References Cited

U.S. PATENT DOCUMENTS

| | | | |
|---|---|---|---|
| 4,641,636 | 2/1987 | Cotrel . | |
| 4,697,582 | 10/1987 | William . | |
| 4,887,595 | 12/1989 | Heinig et al. | 606/61 |
| 5,030,220 | 7/1991 | Howland | 606/61 |
| 5,092,893 | 3/1992 | Smith | 606/60 |
| 5,131,716 | 7/1992 | Plaza | 606/60 |
| 5,181,917 | 1/1993 | Rogozinski | 606/61 |
| 5,242,445 | 9/1993 | Ashman | 606/61 |
| 5,261,909 | 11/1993 | Sutterlin et al. | 606/60 |

OTHER PUBLICATIONS

Danek Medical, *TSRH Crosslink Surgical Technique Manual,* 1990.
Danek Group, *TSRH Spinal System "Shaping the Furture of Spinal Instrumentation"* 1992.

Primary Examiner—Tamara L. Graysay
Attorney, Agent, or Firm—Woodard, Emhardt, Naughton, Moriarty & McNett

[57] ABSTRACT

A spinal system yields a triangular construct across a vertebral body and a quadrilateral construct between vertebral levels. A first pair of screws are engaged in a vertebra on opposite sides of the spinal midline. A longitudinally splined rod, bent into a V-shape, spans between the pair of screws with its vertex generally at the spinal midline. An eyebolt fastener includes a serrated aperture to receive the transverse splined rod, and a threaded post extending through a yoke in the screws. A nut engages the post to clamp eyebolt, rod and yoke together. A second set of fasteners is provided to engage a pair of rigid plates to the transverse rod, each plate spanning between two vertebral levels on either side of the spinal midline. The other end of each plate is engaged to a similar triangular rod construct in the adjacent vertebra.

11 Claims, 2 Drawing Sheets

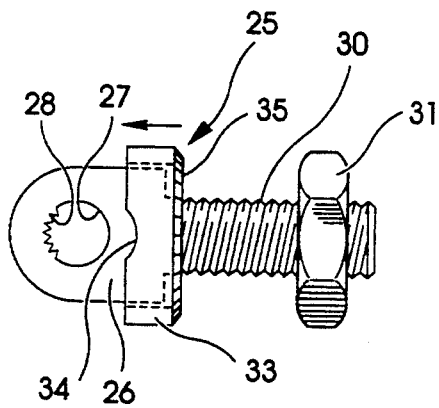
Fig. 5
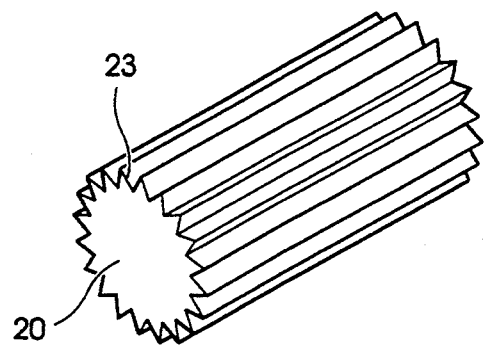
Fig. 3
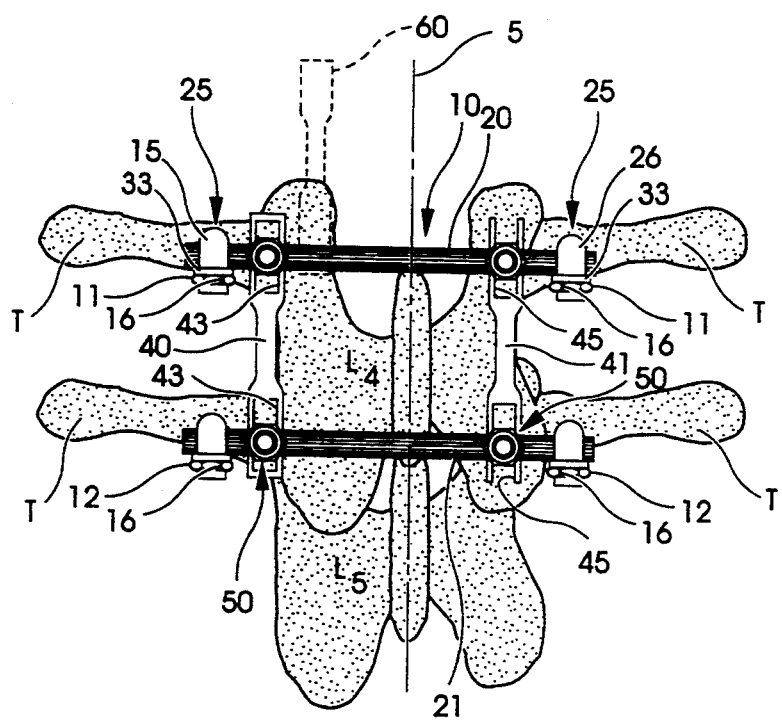
Fig. 1
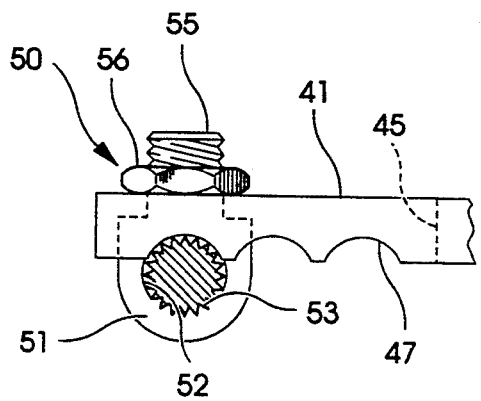
Fig. 6
Fig. 4

TRIANGULAR CONSTRUCT FOR SPINAL FIXATION

BACKGROUND OF THE INVENTION

The present invention broadly concerns devices for use in spinal implant systems, particularly those systems providing fixation at several vertebral levels. More specifically, the invention concerns a novel construct for instrumenting one or more vertebrae, particularly using bone screws for engaging the vertebral body.

Several techniques and systems have been developed for use in correcting and stabilizing spinal curvatures, and for facilitating spinal fusion in the case of spinal disorders or degenerative conditions. In one system, a bendable rod is longitudinally disposed adjacent the vertebral column and is fixed to various vertebrae along the length of the spine by way of a number of fixation elements. Typically two such rod assemblies are used, one on each side of the spinal midline or spinous process.

One example of such a system is the TSRH® Spinal System of Danek Medical, Inc. In this system, hooks or screws are engaged to the spinal rod by way of eyebolts which are slidably disposed on the rod and captured within yokes of the fixation elements. A nut is threaded onto a threaded post of the eyebolt to clamp the yoke and rigidly fix the hook or screw element to the spinal fixation rod. Details of the TSRH® Spinal Implant System are disclosed in the "Surgical Technique Manual" published in 1990 by Danek Medical, Inc., which disclosure is incorporated herein by reference in one construct using the TSRH® Spinal System, a pair of bendable spinal rods extend along the vertebral column of a patient on either side of the sagittal plane. A number of fixation elements, such as hooks or screws, are engaged into several vertebrae, and then are themselves connected to a corresponding spinal rod. A quadrilateral construct is formed by laterally connecting the rods across the sagittal plane. In this instance, generally rigid plates are used to form the lateral connection to help reduce the loss of correction that can occur over time with the use of spinal rod systems of this type.

While the traditional spinal rod system, and systems such as the TSRH® system, have served very well in the past, constructs of this type do not easily lend themselves for instrumentation of only a few vertebral levels. For example, such spinal rod systems are not well suited for fixation of the lower lumbar vertebra to the sacrum of a patient in those instances, spinal plate systems have been provided, such as the Luque plate also sold by Danek Medical. In designs of this type, the plate is directly engaged into a corresponding vertebral body by way of a bone bolt. Plating systems of this type do not readily lend themselves to lateral connection between the plates, and are also limited in the orientation the plates and bone bolts can assume relative to the vertebrae.

There is therefore a need for a spinal fixation construct which is readily adapted for fixation of only a few vertebral levels. The construct needs to be very versatile and easy to implant, while still providing adequate fixation of the vertebral bodies relative to each other.

SUMMARY OF THE INVENTION

In accordance with the invention, a spinal fixation construct is provided for spanning and fixing adjacent vertebral bodies to each other. The construct includes a first pair of spinal screws which are threaded into one vertebral body on opposite sides of the spinal midline. Preferably, each of the spinal screws includes a head portion which is disposed between the spinous process and a transverse process of a lumbar vertebra, for example. The construct includes a longitudinally splined rod which extends laterally between the pair of spinal screws and across the spinal midline. The rod is bent into a generally V-shaped configuration with the vertex of the bend oriented in the middle of the rod and above the spinal midline. Each opposite end of the rod is engaged to a corresponding one of the spinal screws by a pair of fasteners.

In one embodiment, the fasteners comprise eyebolts having an eyebolt body defining an aperture therethrough. The aperture is sized to receive the spinal rod and includes several serrations in a portion of the aperture which are adapted to interdigitate with the splines on the transverse oriented rod. The eyebolt is threaded onto the spinal rod with the serrations engaging some of the splines of the rod to prevent rotation of the eyebolt relative to the rod. The eyebolt also includes a threaded post projecting from the body which is adapted to engage a yoke on the head of each of the spinal screws. A nut is threaded onto the post of the eyebolt to clamp the head of each of the spinal screws to the rod.

The construct further includes a pair of elongated and generally rigid plates which are oriented in the superior/inferior direction adjacent the spinal midline. Each of the plates includes a slot in at least at one end of the plate which is used to engage an eyebolt fastener, similar to the fastener described above. In one embodiment, another pair of spinal screws can engage another vertebral level, such as the sacram, and fasteners can be provided to fix the opposite end of each of the spinal plates to the additional spinal screws. Preferably, the plates are configured to span between only two vertebral levels, such as L5 and S1, with the slot permitting variations in superior/inferior distance between screws.

In another aspect of the invention, each of the spinal screws is a variable angle screw which includes a splined face oriented toward the transverse spinal rod. The fasteners engaging the variable angle screws include a washer having an interdigitating splined face which contacts the splined surface of each of the spinal screws. This feature thus permits the spinal screw to assume a non-perpendicular angle relative to the transverse rod.

In accordance with the present invention, a spinal fixation system is provided which yields a triangular construct at each vertebral level, coupled with a rectangular construct between vertebral bodies. The use of the interdigitating splines between the eyebolt and the transverse rods enhances the fixation and stability of the components, while retaining the simplicity of eyebolts threaded onto the rod found in prior spinal rod systems.

It is therefore one object of the invention to provide a spinal fixation construct which is readily assembled and implanted with a patient, yet retains the strength and durability of other spinal rod systems. A further object is to provide such a construct which is readily adapted for fixation of only a few vertebral levels.

Yet another object resides in a construct that can be expanded to adjacent vertebral levels without requiring a rod spanning all instrumented vertebrae. Other objects and benefits in the invention can be discerned from the following disclosure and accompanying figures.

DESCRIPTION OF THE FIGURES

FIG. 1 is a top elevational view of a spinal fixation construct in accordance with one embodiment of the present invention.

FIG. 3 is a partial view of the transverse rod used with the construct shown in FIG. 1.

FIG. 4 is a side partial cross-sectional view of the engagement between the transverse rod and a plate in the construct shown in FIG. 1.

FIG. 5 is an elevational view of a fastener for use in engaging a fixation screw to the transverse rod shown in the construct of FIG. 1.

FIG. 6 is an elevational view of a portion of a fixation screw used in connection with the construct shown in FIG. 1.

DESCRIPTION OF THE PREFERRED EMBODIMENT

Figure 2:
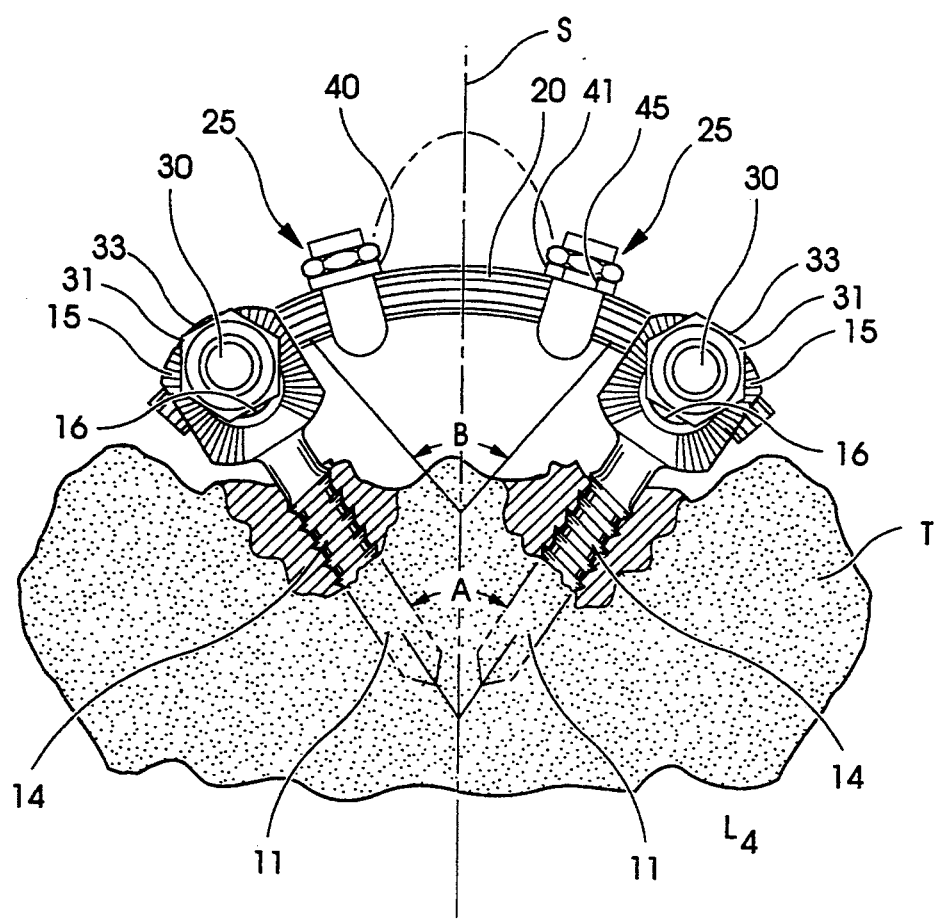
FIG. 2 is an end view of the construct shown in FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring first to FIGS. 1 and 2, the general concept of the spinal fixation construct of the present invention is shown. In these figures, the construct 10 is shown as including a first pair of fixation elements, such as screws 11 which are threaded into a vertebral body, such as the L4 vertebra. The construct in this specific embodiment also includes a second pair of fixation elements or screws 12 engaged into the next lower vertebral level, the L5 vertebra. Each of the fixation screws 11 and 12 include a lower threaded portion 14 which is preferably configured with cancellous threads for engaging the respective vertebral bodies integral with the lower threaded portion 14 is a head portion 15 which is configured to define a yoke 16. In a typical construct, the head portions 15 of each of the screws will be oriented between the spinal midline S and a corresponding transverse process T of the vertebra. Each of the pairs of fixation screws 11, 12 can be engaged into the corresponding vertebral body in a manner known in the art. The fixation screws are oriented at an included angle between the two screws across the sagittal plane, the angle A shown in FIG. 2. The included angle A is generally defined by the physiology of the particular vertebral level to achieve sold fixation without damage to the spinal cord.

The construct 10 further includes a pair of transverse rods, a first rod 20 and a second rod 21, which span the spinal midline S. The first rod 20 spans between the first pair of fixation screws 11, while the second rod is oriented between the second pair of screws 12. Each of the rods 20, 21 is engaged to a corresponding pair of fixation screws 11, 12 by a set of first fasteners 25. The details of the first fastener 25 in accordance with one embodiment of the invention is shown in FIG. 5. In particular, each of the first fasteners 25 includes an eyebolt body 26 which defines a rod aperture 27 sized to receive the transverse rod 20 therethrough. Each of the fasteners includes a threaded post 30 which is configured to extend through the yoke 16 of each of the fixation screws 11, 12. A nut 31 is provided to threadedly engage the post 30 and clamp the eyebolt body 26, rod 20, 21 and fixation screw head portion 15 together.

In one important feature of the invention, the transverse rod 20 includes a longitudinally splined outer surface 23. Similarly, the eyebolt body 25, and particularly the rod aperture 27 defines several serrations 28 which are configured to interdigitate with the splines on the rods 20 and 21. The interdigitation between the splines 23 and the serrations 28 prevents relative rotation between the first fastener 25 and the rod 20 when the construct is finally clamped together.

In another component of the first fastener 25, a washer 33 is provided. The washer fits over the eyebolt body 26 and includes a rod recess 34 which is adapted to contact the surface of one of the spinal rods 20, 21. Opposite the rod recess 34 is a splined face 35 that is configured to interdigitate with a corresponding splined surface 17 on the head portion 15 of each of the fixation screws 11, 12. Thus, the washer 33 performs essentially two functions. In the first function, the rod recess 34 engages and clamps the transverse rod 20, 21 between the serrations 28 and the washer 33. This permits the rod aperture 27 to be large enough so that the eyebolt body 26 can freely rotate around the rod 20 without the splines interdigitating with the serrations to prevent such rotation. Once the eyebolt body is properly oriented relative to the rod, the washer can be moved in the direction of the arrow shown in FIG. 5 toward the rod to clamp the rod in position. A second function served by the washer 33 is to allow the fixation screw 11, 12 to assume a variety of angles relative to the rod. The interdigitation of the spline face 35 and splined surface 17 thus prevents relative rotation between the washer and the fixation screws.

In yet a further important aspect of the fixation construct 10 in accordance with the present Invention, elongated plates 40 and 41 are provided which extend along the superior/inferior direction of the spinal column. The plates can be configured similar to a CROSSLINK ® plate sold by Danek Medical, typically for lateral fixation of a TSRH ® type rod system. In this configuration, each of the plates 40, 41 includes a reduced thickness mid-portion to reduce the space required for the plate. In accordance with the present invention, the plates 40 and 41 can assume slightly modified configurations. In the case of elongated plate 40, a pair of closed slots 43 are provided at each end of the plate. Each of the slots 43 is configured to receive a second fastener, such as fastener 50 shown in FIGS. 1 and 4. Alternatively, the elongated plate 41 includes open slots 45 at one or both ends. In either case, both slots 43 and 45 allow for variation in the superior/inferior distance between the first transverse rod 20 and second transverse rod 21. One advantage of the elongated plate 41 having the open slots 45 is that the plate 41 can be easier to install than the plate having the closed slots 43. In the case of each plate 40, 41, the lower surface of the plates includes a number of parallel grooves 47, extending across the width of each of the plates. These grooves are configured to receive a portion of the transverse rods 20, 21 therein.

The construct 10 includes second fasteners 50 which are adapted to engage each of the elongated plates 40, 41 to the transverse rods 20, 21. The second fasteners 50 are constructed similar to the first fasteners 25, without the addition of the washer 33. In particular, the second fasteners 50 include an eyebolt body 51 defining a rod aperture 52. The rod aperture 52 includes a number of serrations 53 for interdigitating engagement with the spline surface 23 of each of the rods 20, 21. Each second fastener 50 includes a threaded post 55 and a corresponding nut 56. As shown in FIG. 4, the washer 33 of the first fastener 25 is not required because each of the plates 40, 41 serve a corresponding function for engaging the spinal rod clamping between the plate grooves 47 and the eyebolt aperture 52.

In a method in accordance with the present invention, two vertebral bodies, such as the L4 and L5, or L5 and S1 vertebrae, are instrumented with first and second pairs of fixation screws 11 and 12. For the pair of fixation screws 11, a transverse rod 20 is provided which is bent into a V-shaped configuration. The included angle B defined at the vertex of the bent rod 20, is preferably greater than or equal to the included angle A defined by the fixation screws 11 engaged within the vertebral body. In most cases, the included angle B of the bent V-shaped rod 20 will be about 60°. The first fasteners 25 are then threaded onto each end of the bent rod 20 and the rod is oriented across the spinal midline S adjacent each of the fixation screws 11. The threaded post 30 of each of the fasteners 25 is disposed within the yoke 16 of each of the fixation screws and the nut 31 tightened down onto the threaded post 30 to rigidly clamp the head portion 15 of the fixation screw 11 to the corresponding transverse rod 20. A similar procedure is followed with respect to the second pair of fixation screws 12 and the second transverse rod 21 at the next adjacent vertebral level.

In another step of the method, each of the elongated plates 40, 41 is engaged to the rod in the superior/inferior direction. In one implementation of the method, each of the plates 40, 41 is first engaged to the transverse rods prior to implantation of the rods adjacent the fixation screws. In this variation, the second fasteners 40 are threaded onto the rods and loosely clamped to each or the elongated plates 40, 41 to form a generally quadrilateral construct. The slots 43 or 45 in each of the plates allow variation in the distance between the two rods 20, 21 when the rods are being implanted in their proper position adjacent the fixation screws. Some amount of manipulation of the rods then is necessary to orient the first fasteners 25 properly relative to the head portions 15 of the fixation screws 11 and 12.

Alternatively, the second fasteners can be threaded onto the transverse rods, along with the first fasteners. Once the first fasteners are engaged to each of the fixation screws, thereby fixing each of the transverse rod 20, 21 across the spinal midline S, the plates 40, 41 can be attached to the construct. In either case, a rigid quadrilateral frame construct is formed once each of the elongated plates 40, 41 is clamped to the rod by tightening the nuts 56 onto the second fasteners 60. In the preferred embodiment, the elongated plates 40, 41 are clamped to the transverse rods 20, 21 inboard of the engagement of the two fixation screws 11, 12. It can thus be seen that a triangular construct is formed at each vertebral level end a quadrilateral construct formed across the adjacent vertebral levels by the present invention. One measure of versatility of the present system is provided by the transverse rods 20, 21. Specifically, an additional pair of plates, such as plate 60 shown in phantom in FIG. 1, can be engaged to one of the splined transverse rods, such as rod 20. In this manner, a second vertebral level can be instrumented using the same construct. Additional fasteners, such as fasteners 50, can attach the subsequent plates to a transverse rod.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. A spinal fixation construct engaged to the spine of a patient comprising:
   a first pair of bone screws each having a head portion and a lower threaded portion configured for engagement in a vertebral body on opposite sides of the spinal midline with the head portion of each bone screw disposed between the spinous process and a transverse process of the vertebra;
   a first elongated member having a length sufficient to extend laterally across the spinal midline, said member bent into a V-shaped configuration with a vertex generally in the middle of said member;
   a pair of first fasteners each engaging corresponding opposite ends of said elongated member to the head portion of a corresponding one of said first pair of bone screws such that said vertex is generally aligned with said spinal midline;
   a pair of elongated plates having one end and an opposite end, said plates configured to be oriented in the superior/inferior direction on opposite sides of the spinal midline; and
   a pair of second fasteners each clamping said elongated member to said one end of a corresponding one of said pair of elongated plates.

2. The spinal fixation construct of claim 1, wherein:
   said head portion of each of said pair of bone screws includes a splined surface; and
   each of said pair of first fasteners includes an interdigitating splined face for mating with said splined surface of a corresponding one of said pair of bone screws to prevent relative rotation between the bone screw and the fastener.

3. The spinal fixation construct of claim 1, wherein:
   said elongated member is a rod includes longitudinal splines defined around the circumference of said rod; and
   each of said pair of first fasteners and said pair of second fasteners includes an eyebolt having a body defining an aperture for receiving said elongated rod therethrough, said aperture having a plurality of serrations defined therein for mating with said longitudinal splines of said elongated rod to prevent relative rotation between said rod and said eyebolt.

4. The spinal fixation construct of claim 1, wherein each of said pair of elongated plates is engagable to said elongated member between the spinal midline and a corresponding one of said pair of first fasteners.

5. The spinal fixation construct of claim 1, wherein:
   each of said pair of elongated plates defines a slot at said one end of said plates; and each of said pair of second fasteners includes a portion configured to extend through said slot of a corresponding one of said plates for engagement of said fasteners thereto at variable superior/inferior locations.

6. The spinal fixation construct of claim 1, further comprising:
- a second pair of bone screws each having a head portion and a lower threaded portion configured for engagement into a second vertebral body on opposite sides of the spinal midline;
- a second elongated member having a length sufficient to extend laterally across the spinal midline;
- a pair of third fasteners identical to said pair of first fasteners each clamping said second elongated member to the head portion of a corresponding one of said second bone screws; and
- a pair of fourth fasteners identical to said pair of second fasteners each engaging said second elongated member to said opposite end of a corresponding one of said pair of elongated plates.

7. The spinal fixation construct of claim 6, wherein:
- each of said first and second elongated members is a rod which includes longitudinal splines defined around the circumference of each rod; and
- each of said pair of first, second, third and fourth fasteners includes an eyebolt having a body defining an aperture for receiving one of said elongated rods therethrough, said aperture having a plurality of serrations defined therein for mating with said longitudinal splines of the elongated rod to prevent relative rotation between the rod and said eyebolt.

8. The spinal fixation construct of claim 6, wherein:
each of said pair of elongated plates defines a slot at said one end of said plates; and each of said pair of second fasteners includes a portion configured to extend through said slot of a corresponding one of said plates for engagement of said fasteners thereto at variable superior/inferior locations.

9. The spinal fixation construct of claim 8, wherein:
each of said pair of elongated plates further defines a slot at said opposite end of said plates; and each of said pair of fourth fasteners includes a portion configured to extend through said slot of a corresponding one of said plates for engagement of said fasteners thereto at variable superior/inferior locations.

10. A method for instrumenting the spine comprising the steps of:
- implanting a pair of bone screws into a vertebral body with the head of each screw disposed between the spinal midline and a corresponding transverse process of the vertebra, the axes of the pair of bone screws defining an included angle in the lateral plane;
- bending an elongated member into a V-shaped configuration with an included angle at the vertex of the member greater than or equal to the included angle between the pair of bone screws;
- engaging the member to the head of each of the pair of bone screws with the vertex of the member arranged generally at the spinal midline; engaging one end of a pair of elongated plates to the member at a location apart from the bone screw and with the plates arranged on opposite sides of the spinal midline and extending in the superior/inferior direction; and
- fastening an opposite end of the pair of plates to another vertebral body.

11. The method for instrumenting the spine of claim 10, wherein:
- the elongated member is a rod which includes a plurality of longitudinal splines around the circumference of the rod;
- the head of each of the bone screws includes a slot defined therein; and
- the step of engaging the member to the head of the bone screws includes;
- sliding a pair of eyebolts onto each rod, the eyebolt defining an aperture with serrations therein for interdigitating with the splines on the rod to prevent relative rotation therebetween, each eyebolt further having a threaded post projecting therefrom;
- orienting each eyebolt on the rod with the serrations interdigitating with the splines an extending the threaded post through the slot in the head of a corresponding bone screw; and
- tightening a nut onto each threaded post to clamp the head of the bone screw to the rod.

* * * * *